(12) United States Patent
Wijdenes et al.

(10) Patent No.: US 7,452,981 B2
(45) Date of Patent: Nov. 18, 2008

(54) HUMANIZED ANTI-CD4 ANTIBODY WITH IMMUNOSUPPRESSIVE PROPERTIES

(75) Inventors: John Wijdenes, Larnod (FR); Helmut Jonuleit, Ginsheim-Gustavsburg (DE)

(73) Assignee: Biotest AG, Dreieich (DE)

( * ) Notice: Subject to any disclaimer, the term of this patent is extended or adjusted under 35 U.S.C. 154(b) by 0 days.

(21) Appl. No.: 11/217,402

(22) Filed: Sep. 2, 2005

(65) Prior Publication Data

US 2006/0051346 A1    Mar. 9, 2006

Related U.S. Application Data

(63) Continuation of application No. PCT/EP2004/002888, filed on Mar. 19, 2004.

(30) Foreign Application Priority Data

Mar. 21, 2003  (EP) .................................. 03290725
Apr. 16, 2003  (EP) .................................. 03290942

(51) Int. Cl.
    *C07K 16/28* (2006.01)
(52) U.S. Cl. ............................. 530/388.75; 424/154.1
(58) Field of Classification Search ........................ None
    See application file for complete search history.

(56) References Cited

U.S. PATENT DOCUMENTS 5,777,085 A * 7/1998 Co et al. ................. 530/388.23

FOREIGN PATENT DOCUMENTS

EP      1 241 249       9/2002
WO      WO 91/09966     7/1991

OTHER PUBLICATIONS

Racadot et. al. Immunological follow-up of 17 patients with rheumatoid arthritis treated in vivo with an anti-T CD4+ monoclonal antibody (B-F5). Clinical and Experimental Rheumatology. 1992; 10: 365-374.*
Rudikoff et. al. Single amino acid substitution altering antigen-binding specificity. Proc. Natl. Acad. Sci. 1982; 79: 1979-1983.*
Panka et. al. Variable region framework differences results in decreased or increased affinity of variant anti-digoxin antibodies. Proc. Natl. Acad. Sci. 1988; 85: 3080-3084.*
Bartholomew, M.; et al., "Functional analysis of the effects of a fully humanized anti-CD4 antibody on resting and activated human T cells," Immunology 1995;85(1):41-48.
Racadot, E., et al., "Immunological follow-up of 17 patients with rheumatoid arthritis treated in vivo with an anti-T CD4+ monoclonal antibody (B-F5)," Clin. Exp. Rheumatol. 1992;10:365-374.
International Search Report for PCT/EP2004/002888 (Aug. 5, 2004).
International Preliminary Examination Report for PCT/EP2004/002888 (Jan. 12, 2005).
Boshart, M., et al., "A Very Strong Enhancer Is Located Upstream of an Immediate Early Gene of Human Cytomegalovirus," Cell 1985;41:512-530.

Canva-Delcambre, V., et al., "Treatment of severe Crohn's disease with anti-CD4 monoclonal antibody," Aliment. Pharmacol. Ther. 1996;10:721-727.
Chothia, C., et al., "Conformation of immunoglobulin hypervariable regions," Nature 1989;342:877-883.
Chothia, C., et al., "Canonical Structures for the Hypervariable Regions of Immunoglobulins," J. Mol. Biol. 1987;196:901-917.
Cohen, J. L., et al., "CD4+CD25+ Immunoregulatory T Cells: New Therapeutics for Draft-Versus-Host Disease," J. Exp. Med. 2002;196(3):401-406.
Coloma, M. J., et al., "Primer Design for the Cloning of Immunoglobulin Heavy-Chain Leader-Variable Regions from Mouse Hybridoma Cells Using the PCR," BioTechniques 1991;11(2):152-156.
Dantal, J., et al., "Anti-CD4 MoAb Therapy in Kidney Transplantation—A Pilot Study in Early Prophylaxis of Rejection," Transplantation 1996;62(10):1502-1506.
Darby, C. R., et al., "Nondepleting Anti-CD4 Antibodies in Transplantation," Transplant. 1994;57(10):1419-1426.
Dieckmann, D., et al., "Ex Vivo Isolation and Characterization of CD4+CD25+ T cells with Regulatory Properties from Human Blood," J. Exp. Med. 2001;193(11):1303-1310.
Edmundson, A. B., et al., "A Search for Site-Filling Ligands in the Mcg Bence-Jones Dimer: Crystal Binding Studies of Fluorescent Compounds," Mol. Immunol. 1984;21(7):561-576.
Felgner, P. L., et al., "Lipofection: A highly efficient, lipid-mediated DNA-transfection procedure," Proc. Natl. Acad. Sci. USA 1987;84:6413-7417.
Foote, J., et al., "Antibody Framework Residues Affecting the Conformation of the Hypervariable Loops," J. Mol. Biol. 1992;224:487-499.
Gillies, S. D., et al., "A Tissue-specific Transcription Enhancer Element Is Located in the Major Intron of a Rearranged Immunoglobulin Heavy Chain Gene," Cell 1983;33:717-728.
Goetzl, E. J., et al., "Affinity Labeling of a Mouse Myeloma Protein Which Binds Nitrophenyl Ligands. Kinetics of Labeling and Isolation of a Labeled Peptide," Biochemistry 1970;9(5):1267-1278.
Goldberg, D., et al., "Immunological Effects of High Dose Administration of Anti-CD4 Antibody in Rheumatoid Arthritis Patients," J. Autoimmun. 1991;4:617-630.
Gorman, C. M., et al., "The Rous sarcoma virus long terminal repeat is a strong promoter when introduced into a variety of eukaryotic cells by DNA-mediated transfection," Proc. Natl. Acad. Sci. USA 1982;79:6777-6781.
Gorman, S. D., et al., "Reshaping a therapeutic CD4 antibody," Proc. Natl. Acad. Sci. USA 1991;88:4181-4185.

(Continued)

*Primary Examiner*—Michail Belyavskyi
*Assistant Examiner*—Zachary Skelding
(74) *Attorney, Agent, or Firm*—Shelly Guest Cermak; Cermak, Kenealy & Vaidya LLP

(57) ABSTRACT

A humanized antibody derived from mouse monoclonal anti-CD4 antibody B-F5 is able to activate CD25+CD4+ regulatory T cells and is useful for preparing immunosuppressive compositions.

4 Claims, 9 Drawing Sheets

OTHER PUBLICATIONS

Gottlieb, A. B., et al., "Anti-CD4 monoclonal antibody treatment of moderate to severe psoriasis vulgaris: Results of a pilot, multicenter, multiple-dose placebo-controlled study," J. Am. Acad. Dermatol. 2000;43:595-604.

Graham, F. L., et al., "A New Technique for the Assay of Infectivity of Human Adenovirus 5 DNA," Virology 1973;52:456-467.

Hoffmann, P., et al., "Donor-type $CD4^+CD25^+$ Regulatory T Cells Suppress Lethal Acute Graft-Versus-Host Disease after Allogenic Bone Marrow Transplantation," J. Exp. Med. 2002;196(3):389-399.

Jonuleit, H., et al., "Identification and Functional Characterization of Human $CD4^+CD25^+$ T Cells with Regulatory Properties Isolated from Peripheral Blood," J. Exp. Med. 2001;193(11):1285-1294.

Kabat, E. A., "Structure and Heterogeneity of Antibodies," Proc. 10th Congr. Eur. Soc. Haematl., Strasbourg Acta haemat. 1966;36:198-238.

Kettleborough, C. A., et al., "Humanization of a mouse monoclonal antibody by CDR-grafting: the importance of framework residues on loop conformation," Protein Eng. 1991;4(7):773-783.

Levings, M. K., et al., "Human $CD4^+CD25^+$ T Regulatory Cells Suppress Naïve and Memory T Cell Proliferation and Can Be Expanded In Vitro without Loss of Function," J. Exp. Med. 2001;193(11):1295-1301.

Lusky, M., et al., "Inhibition of SV40 replication in simian cells by specific pBR322 DNA sequences," Nature 1981;293:79-81.

Morel, P., et al., "Anti-CD4 Monoclonal Antibody Administration in Renal Transplanted Patients," Clin. Immunol. Immunopath. 1990;56:311-322.

Morel, P., et al., "Anti-CD4 Monoclonal Antibody Therapy in Severe Psoriasis," J. Autoimmun. 1992;5:465-477.

Mount, D. W., et al., "Microcomputer programs for back translation of protein to DNA sequences and analysis of ambiguous DNA sequences," Nucl. Acids Res. 1984;21(1):819-823.

Orlandi, R., et al., "Cloning immunoglobulin variable domains for expression by the polymerase chain reaction," Proc. Natl. Acad. Sci. USA 1989;86:3833-3837.

Osterburg, G., et al., "Computer programs for the analysis and the management of DNA sequences," Nucl. Acids Res. 1982;10(1):207-216.

Potter, H., et al., "Enhancer-dependent expression of human κ immunoglobulin genes introduced into mouse pre-B lymphocytes by electroporation," Proc. Natl. Acad. Sci. USA 1984;81:7161-7165.

Puls, R. L., et al., "Gene transfer and expression of a non-viral polycation-based vector in $CD4^+$ cells," Gene Ther. 1999;6:1774-1778.

Racadot, E., et al., "Treatment of Multiple Sclerosis with Anti-CD4 Monoclonal Antibody," J. Autoimmun. 1993;6:771-786.

Reczko, M., et al., "Prediction of hypervariable CDR-H3 loop structures in antibodies," Protein Eng. 1995;8(4):389-395.

Rep. M. H. G., et al., "Treatment with Depleting CD4 Monoclonal Antibody Results in a Preferential Loss of Circulating Naïve T Cells but Does Not Affect IFN-γ Secreting TH1 Cells in Humans," J. Clin. Invest. 1997;99(9):2225-2231.

Rumbach, L., et al., "Biological assessment and MRI monitoring of the therapeutic efficacy of a monoclonal anti-T CD4 antibody in multiple sclerosis patients," Multiple Sclerosis 1996;1:207-212.

Saitovitch, D., et al., "Kinetics of Induction of Transplantation Tolerance With a Nondepleting Anti-Cd4 Monoclonal Antibody and Donor-Specific Transfusion Before Transplantation: A Critical Period of Time Is Required for Development of Immunological Unresponsiveness," Transplant. 1996;61(11):1642-1647.

Sakaguchi, S., et al., "Immunologic Self-Tolerance Maintained by Activated T Cells Expressing IL-2 Receptor α-Chains (CD25)," J. Immunol. 1995;155:1151-1164.

Sastry, L., et al., "Cloning of the immunological repertoire in Escherichia coli for generation of monoclonal catalytic antibodies: Construction of a heavy chain variable region-specific cDNA library," Proc. Natl. Acad. Sci. USA 1989;86:5728-5732.

Schimke, R. T., "Gene Amplification in Cultured Animal Cells," Cell 1984;37:705-713.

Shevach, E. M., "Certified Professionals: $CD4^+CD25^+$ Suppressor T Cells," J. Exp. Med. 2001;193(II):F41-F45.

Skov, L., et al., "HuMax-CD4 A Fully Human Monoclonal Anti-CD4 Antibody for the Treatment of Psoriasis Vulgaris," Arch. Dermatol. 2003;139:1433-1439.

Southern, P. J., et al., "Transformation of Mammalian Cells to Antibiotic Resistance with a Bacterial Gene Under Control of the SV40 Early Region Promoter," J. Mol. Appl. Genetics 1982;1:327-341.

Subramani, S., et al., "Expression of the Mouse Dihydrofolate Reductase Complementary Deoxyribonucleic Acid in Simian Virus 40 Vectors," Mol. Cell. Biol. 1981;1(9):854-864.

Tak, P. P., et al., "Reduction of Synovial Inflammation After Anti-CD4 Monoclonal Antibody Treatment in Early Rheumatoid Arthritis," Arth. Rheum. 1995;38(1):1457-1465.

Takahashi, T., et al., "Immunologic self-tolerance maintained by $CD4^+CD25^+$ naturally anergic and suppresive T cells: induction of autoimmune disease by breaking their anergic/suppressive state," Internatl. Immunol. 1998;10(12):1969-1980.

Taylor, P. A., et al., "The infusion of ex vivo activated and expanded $CD4^+CD25^+$ immune regulatory cells inhibits graft-versus-host disease lethality," Blood 2002;99(10):3493-3499.

Thornton, A. M., et al., "Suppressor Effector Function of $CD4^+CD25^+$ Immunoregulatory T Cells Is Antigen Nonspecific," J. Immunol. 2000;164:183-190.

Vieira, J., et al., "Production of Single-Stranded Plasmid DNA," Methods Enzymol. 1987;153:3-11.

Ward, S., et al., "Binding activities of a repertoire of single immunoglobulin variable domains secreted from Escherichia coli," Nature 1989;341:544-546.

Wendling, D., et al., "Treatment of Rheumatoid Arthritis with Anti CD4 Monoclonal Antibody. Open Study of 25 Patients with the B-F5 Clone," Clin. Rheumatol. 1992;11(4):542-547.

Wendling, D., et al., "A Randomized, Double Blind, Placebo Controlled Multicenter Trial of Murine Anti-CD4 Monoclonal Antibody Therapy in Rheumatoid Arthritis," J. Rheumatol. 1998;25(8):1457-1461.

Zhu, Z., et al., "Inhibition of human leukemia in an animal model with human antibodies directed against vascular endothelial growth factor 2. Correlation between antibody affinity and biological activity," Leukemia 2003;17:604-611.

\* cited by examiner mB-F5 V$_H$ :

CAG GAA TAC CTT GTG GAG ACC GGG GGA GGC TTG GTG AGG CCT GGA AAT TCT CTG AAA

CTC TCC TGT GTC ACC TCG GGT TTC AGT TTC AGT GAC TGC CGG ATG TAC TGG CTT CGC

CAG CCT CCA GGG AAG GGG CTG GAG TGG ATT GGT GTG ATT TCA GTC AAA TCT GAG AAT

TAT GGA GCA AAT TAT GCA GAG TCT GTG AGG GGC AGA TTC ACT ATT TCA AGA GAT GAT

TCA AAA AGC AGT GTC TAT CTG CAG ATG AGC AGA TTG AGA GAG GAA GAC ACT GCC ACT

TAT TAT TGT AGT GCC TCC TAT TAT AGG TAC GAC GTG GGG GCC TGG TTT GCT TAC TGG

GGC CAA GGG ACT CTG GTC ACT GTC TCT GCA

Figure 1 mB-F5 V$_K$ :

GAC ATT GTG CTG ACA CAG TCT CCT TCT TCC TTA GTT GTA TCT CTG GGG CAG AGG GCC

ACC ATC TCA TGC AGG GCC AGC AAA AGT GTC AGT ACA TCT GGC TAC AGT TAT ATA TAT

TGG TAC CAA CAG ATC CCA GGA CAG CCA CCC AAA CTC CTC ATC TAT CTT GCA TCC ATC

CTA GAA TCT GGG GTC CCT GGC AGG TTC AGT GGC AGT GGG TCT GGG ACA GAC TTC ACC

CTC AAC ATC CAT CCT GTG GAG GAG GAG GAT GCT GCA ACC TAT TAC TGT CAG CAC AGT

AGG GAA CTT CCG TGG ACG TTC GGT GGA GGC ACC AAG CTG GAG ATC AAA CGG GCT GAT

GCT GCA CCA ACT GTA TCC ATC TTC CCA CCA TCC AGT GAG CA

Figure 2

```
              FR1                CDR1              FR2
           1         2             3              4
       12345678901234567890123 4567777789012345 67890123456789
                                   ABCD mB-F5    DIVLTQSPSSLVVSLGQRATISC  RASKSVSTSGYSYIY  WYQQIPGQPPKLLIY
hB-F5L4M DIVMTQSPDSLAVSLGERATINC  RASKSVSTSGYSYIY  WYQQKPGQPPKLLIY
hB-F5L4L ---L-------------------  ---------------  ---------------
FK-001   DIVMTQSPDSLAVSLGERATINC                   WYQQKPGQPPKLLIY

CDR2              FR3
         5      6          7           8
       012345 6 789012345678901234567890123456 78 mB-F5    LASILES  GVPCRFSGSGSGTDFTLNIHPVEEEDAATYYC
hB-F5L4M LASILES  GVPDRFSGSGSGTDFTLTISSLQAEDVAVYYC
hB-F5L4L -------  --------------------------------
FK-001            GVPDRFSGSGSGTDFTLTISSLQAEDVAVYYC

CDR3      FR4
         9         10
       901234567 8901234567 mB-F5    QHSRELPWT  FGGGTKLEIK
hB-F5L4M QHSRELPWT  FGQGTKVEIK
hB-F5L4L ---------  F---------
FK-001              FGQGTKVEIK
```

Figure 3

```
                    FR1                          CDR1      FR2
            1               2         3                     4
            12345678901234567890123456789012345 67890123456789 mB-F5       QEYL.VETGGGLVRPGNSLKLSCVTSGFSFS    DCRMY  WLRQPPGKGLEWIG
hB-F5H37V   EEQLVESGGGLVKPGGSLRLSCAASGFSFS    DCRMY  WVRQAPGKGLEWIG
hB-F5H37L   ------------------------------    -----  ----L---------
M2G         EVQLVESGGGLVKPGGSLRLSCAASGFTFS            WVRQAPGKGLEWVG

CDR2                           FR3
            5              6          7                   8                    9
            012222345678901234 5   67890123456789012222345678901234
                ABC                                       ABC mB-F5       VISVKSENYGANYAESVRG   KFTISRDDSKSSVYLQMSRLREEDTATYYCSA
hB-F5H37V   VISVKSENYGANYAESVRG   RFTISRDDSKNTVYLQMNSLRTEDTAVYYCSA
hB-F5H37L   -------------------   --------------------------------
M2G                               RFTISRDDSKNTLYLQMNSLKTEDTAVYYCTT

CDR3          FR4
                10             11
            5678900000012  34567890123
                ABCDE mB-F5       SYYRYDVGAWFAY  WGQGTLVTVSA
hB-F5H37V   SYYRYDVGAWFAY  WGQGTLVTVSS
hB-F5H37L   -------------  -----------
M2G                        WGQGTLVTVSS
```

Figure 4

```
GA GGA GCT CCA GAC AAT GTC TGT CTC CTT CCT CAT CTT CCT GCC CGT GCT GGG CCT

CCC ATG GGG TCA GTG TCA GGG AGA TGC CGT ATT CAC AGC AGC ATT CAC AGA CTG AGG

GGT GTT TCA CTT TGC TGT TTC CTT TTG TCT CCA GGT GTC CTG TCA GAG GAA CAG CTT
                                                            E   E   Q   L

GTG GAG TCT GGG GGA GGC TTG GTG AAA CCC GGA GGT TCT CTG AGG CTC TCC TGT GCA
 V   E   S   G   G   G   L   V   K   P   G   G   S   L   R   L   S   C   A

GCC TCG GGT TTC AGT TTC AGT GAC TGC CGG ATG TAC TGG GTT CGC CAG GCT CCA GGG
 A   S   G   F   S   F   S   D   C   R   M   Y   W   V   R   Q   A   P   G

AAG GGG CTG GAG TGG ATT GGT GTG ATT TCA GTC AAA TCT GAG AAT TAT GGA GCA AAT
 K   G   L   E   W   I   G   V   I   S   V   K   S   E   N   Y   G   A   N

TAT GCA GAG TCT GTG AGG GGC AGA TTC ACT ATT TCA AGA GAT GAT TCA AAA AAC ACG
 Y   A   E   S   V   R   G   R   F   T   I   S   R   D   D   S   K   N   T

GTC TAT CTG CAG ATG AAC AGC TTG AAG ACC GAA GAC ACT GCC GTT TAT TAT TGT AGT
 V   Y   L   Q   M   N   S   L   K   T   E   D   T   A   V   Y   Y   C   S

GCC TCC TAT TAT AGG TAC GAC GTG GGG GCC TGG TTT GCT TAC TGG GGC CAA GGG ACT
 A   S   Y   Y   R   Y   D   V   G   A   W   F   A   Y   W   G   Q   G   T

CTG GTC ACT GTC TCT TCA GGT AAG AAT GGC CAA GCT TG
 L   V   T   V   S   S
```

Figure 5

GGA GGA TCC AAT TAT CTG CTG ACT TAT AAT ACT ACT AGA AAG CAA ATT TAA ATG ACA

TAT TTC AAT TAT ATC TGA GAC AGC GTG TAT AAG TTT ATG TAT AAT CAT TGT CCA TTC

| CTG | ACT | ACA | GGT | GCC | TAC | GGG | GAC | ATC | GTG | ATG | ACC | CAG | TCT | CCA | GAC | TCC | CTG | GCT |
|-----|-----|-----|-----|-----|-----|-----|-----|-----|-----|-----|-----|-----|-----|-----|-----|-----|-----|-----|
|     |     |     |     |     |     |     | D   | I   | V   | M   | T   | Q   | S   | P   | D   | S   | L   | A   |

| GTG | TCT | CTG | GGC | GAG | AGG | GCC | ACC | ATC | AAC | TGC | AGG | GCC | AGC | AAA | AGT | GTC | AGT | ACA |
|-----|-----|-----|-----|-----|-----|-----|-----|-----|-----|-----|-----|-----|-----|-----|-----|-----|-----|-----|
| V   | S   | L   | G   | E   | R   | A   | T   | I   | N   | C   | R   | A   | S   | K   | S   | V   | S   | T   |

| TCT | GGC | TAC | AGT | TAT | ATA | TAT | TGG | TAC | CAG | CAG | AAA | CCA | GGA | CAG | CCT | CCT | AAG | CTG |
|-----|-----|-----|-----|-----|-----|-----|-----|-----|-----|-----|-----|-----|-----|-----|-----|-----|-----|-----|
| S   | G   | Y   | S   | Y   | I   | Y   | W   | Y   | Q   | Q   | K   | P   | G   | Q   | P   | P   | K   | L   |

| CTC | ATT | TAC | CTT | GCA | TCC | ATC | CTA | GAA | TCT | GGG | GTC | CCT | GAC | CGA | TTC | AGT | GGC | AGC |
|-----|-----|-----|-----|-----|-----|-----|-----|-----|-----|-----|-----|-----|-----|-----|-----|-----|-----|-----|
| L   | I   | Y   | L   | A   | S   | I   | L   | E   | S   | G   | V   | P   | D   | R   | F   | S   | G   | S   |

| GGG | TCT | GGG | ACA | GAT | TTC | ACT | CTC | ACC | ATC | AGC | AGC | CTG | CAG | GCT | GAA | GAT | GTG | GCA |
|-----|-----|-----|-----|-----|-----|-----|-----|-----|-----|-----|-----|-----|-----|-----|-----|-----|-----|-----|
| G   | S   | G   | T   | D   | F   | T   | L   | T   | I   | S   | S   | L   | Q   | A   | E   | D   | V   | A   |

| GTT | TAT | TAC | TGT | CAG | CAC | AGT | AGG | GAA | CTT | CCG | TGG | ACG | TTC | GGC | CAA | GGG | ACC | AAG |
|-----|-----|-----|-----|-----|-----|-----|-----|-----|-----|-----|-----|-----|-----|-----|-----|-----|-----|-----|
| V   | Y   | Y   | C   | Q   | H   | S   | R   | E   | L   | P   | W   | T   | F   | G   | Q   | G   | T   | K   |

| GTG | GAA | ATC | AAA | CGT | GAG | TAG | AAT | TTA | AAT | TTT | AAG | CTT | CTT |
|-----|-----|-----|-----|-----|-----|-----|-----|-----|-----|-----|-----|-----|-----|
| V   | E   | I   | K   |     |     |     |     |     |     |     |     |     |     |

Figure 6

HUMANIZED ANTI-CD4 ANTIBODY WITH IMMUNOSUPPRESSIVE PROPERTIES

This application is a continuation of, and claims priority under 35 U.S.C. § 120 to, International application number PCT/EP2004/002888, filed 19 Mar. 2004, and claims priority under 35 U.S.C. § 119 to European application no. 03.290725.5, filed 21 Mar. 2003, and European application no. 03.290942.6, filed 16 Apr. 2003, the entirety of each of which is incorporated by reference herein.

BACKGROUND OF THE INVENTION

1. Field of the Invention

The invention relates to a humanized anti-CD4 antibody, and to its use for immunomodulation.

2. Brief Description of the Related Art

Autoimmune diseases as well as graft rejection result from an inappropriate immune response to tissue antigens: self antigens in the first case, and allograft antigens in the second one.

Autoimmune diseases include for instance rheumatoid arthritis, type I diabetes, multiple sclerosis, Crohn's disease, ulcerative colitis, atopic dermatitis, etc.

Conventional treatments for these immunological disorders involve immunosuppressive drugs. However these drugs induce a general immunosuppression, resulting in inhibition of not only the harmful functions of the immune system, but also the useful ones. As a consequence, they induce side effects, such as opportunistic infections.

As an alternative approach, it has been proposed to use immunosuppressive monoclonal antibodies (mAbs) against cell-surface molecules, in order to remove specific lymphocyte subsets (depleting antibodies) or to inhibit the function of a target surface molecule without killing the cell bearing it (nondepleting-antibodies).

It is generally agreed that CD4+ T cells play a major part in initiating and maintaining autoimmunity. Accordingly, it has been proposed to use mAbs against CD4+ T cells surface molecules, and in particular anti-CD4mAbs, as immunosuppressive agents. Although numerous clinical studies confirmed the potential interest of this approach, they also raised several issues to be addressed in order to make anti-CD4mAbs more suitable for use in routine clinical practice.

By way of example, B-F5 antibody (murine IgG1 anti-human CD4) was tested in different autoimmune diseases:

in rheumatoid arthritis patients, several open studies suggested a positive clinical effect of B-F5 at a daily dose of at least 20 mg (Racadot et al. Clin. Exp. Rheumatol. 10 (4): 365-74; 1992; Wendling et al., Clin. Rheumatol., 11 (4): 542-7, 1992). However, the results observed in a placebo controlled trial with a daily dose of 20 mg for 10 days did not show a significant improvement (Wendling et al. J. Rheumatol.; 25 (8): 1457-61, 1998).

in psoriasis, an improvement in psoriatic lesions was observed following a treatment at a dose of 0.2 mg/kg/day to 0.8 mg/kg/day for 7 or 8 days (Morel et al. J. Autoimmun., 5 (4): 465-77, 1992);

in multiple sclerosis (MS) patients, some positive effects were observed after a 10 days treatment in patients with relapsing-remitting forms, some of who were relapse-free at the 6th month post-therapy (Racadot et al., J. Autoimmun., 6 (6): 771-86, 1993); similar effects were observed by Rumbach et al. (MultScler; 1 (4): 207-12, 1996);

in severe Crohn's disease, no significant improvement was observed in patients receiving B-F5 at a dose of 0.5 mg/day/kg for 7 consecutive days or of 0.5 mg/day/kg on the first day (day 0) and of 1 mg/day/kg on days 1-6(Canva-Delcambre et al., Aliment Pharmacol. Ther. (5): 721-7, 1996);

in prevention of allograft rejection, a modification of the biological parameters, indicating an action of B-F5 in vivo at a 30 mg/daily dose was reported. However, it was reported that B-F5 bioavailability was not sufficient to allow its use for prophylaxis of allograft rejection (Dantal et al. Transplantation, 27; 62(10): 1502-6, 1996).

It appears from the above that a first issue to be solved is the need of using high doses of mAb to obtain a clinical improvement. This may result inter alia from the poor accessibility to the mAb of the lymphocytes in the target tissues. The use of higher doses may result in an excessive action on blood lymphocytes, inducing unwanted side effects.

Another drawback of therapy with monoclonal antibodies in humans is that these antibodies are generally obtained from mouse cells, and provoke antimouse responses in the human recipients. This not only results in a lesser efficiency of the treatment and even more of any future treatment with mouse monoclonal antibodies, but also in an increased risk of anaphylaxis.

This drawback can, in principle, be avoided by the use of humanized antibodies, obtained by grafting the complementarity-determining regions (CDRs) of a mouse monoclonal antibody, which determine the antigen-binding specificity, onto the framework regions (FRs) of a human immunoglobulin molecule. The aim of humanization is to obtain a recombinant antibody having the same antigen-binding properties as the mouse monoclonal antibody from which the CDR sequences were derived, and far less immunogenic in humans.

In some cases, substituting CDRs from the mouse antibody for the human CDRs in human frameworks is sufficient to transfer the antigen-binding properties (including not only the specificity, but also the affinity for antigen). However, in many antibodies, some FR residues are important for antigen binding, because they directly contact the antigen in the antibody-antigen complex, or because they influence the conformation of CDRs and thus their antigen binding performance.

Thus, in most cases it is also necessary to substitute one or several framework residues from the mouse antibody for the human corresponding FR residues. Since the number of substituted residues must be as small as possible in order to prevent anti-mouse reactions, the issue is to determine which amino acid residue (s) are critical for retaining the antigen-binding properties. Various methods have been proposed for predicting the more appropriate sites for substitution. Although they provide general principles that may be of some help in the first steps of humanization, the final result varies from an antibody to another. Thus, for a given antibody, it is very difficult to foretell which substitutions will provide the desired result.

BRIEF DESCRIPTION OF THE DRAWINGS

FIG. 1 depicts a DNA sequence encoding mouse B-F5 $V_H$ region.

FIG. 2 depicts a DNA sequence encoding mouse B-F5 $V_K$ region.

FIG. 3 shows an alignment of the polypeptide sequences of B-F5, FK-001, L4L, and L4M.

FIG. 4 shows an alignment of the polypeptide sequences of B-F5, M26, H37L, and H37V.

FIG. 5 depicts the fragment of the plasmid encoding the VH region of humanized BF-5.

FIG. 6 depicts the fragment of the plasmid encoding the VK region of humanized BF-5.

DETAILED DESCRIPTION OF THE INVENTION

Figure 7:
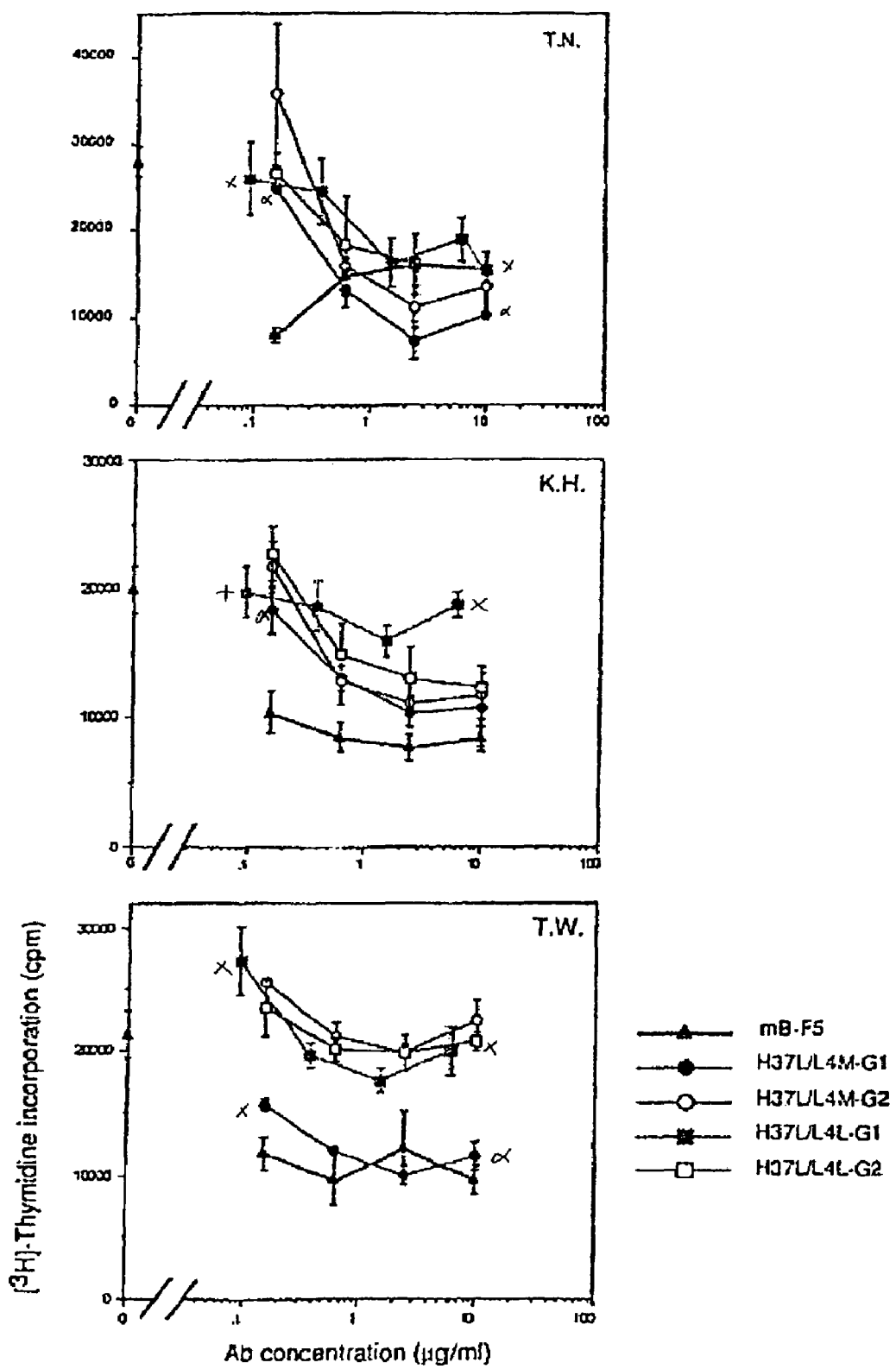
FIG. 7 shows the results of the ELISA assays, wherein murine and hB-F5s could moderately inhibit ConA-induced proliferation, but the activities varied from antibody to antibody and/or from donor to donor.

The inventors have however attempted the humanization of mouse B-F5, and have succeeded in producing humanized B-F5 (hereinafter referred to as hB-F5) having the same CD4 binding properties than parent mouse B-F5.

Furthermore, they have found that, surprisingly, hB-F5 has an in vivo optimal immunosuppressive effect at far lower doses than those previously used with parent B-F5, and than those currently used with other anti-CD4 monoclonal antibodies.

Actually, the inventors have observed that hB-F5 provided an effective immunosuppression, reflected by a positive clinical effect in rheumatoid arthritis patients, when used in a 10 days treatment at a dose as low as 1 mg/day, and preferably at a dose of 5 mg every second day.

The present invention provides a humanized antibody (hB-F5) derived from mouseB-F5 MAb, wherein said hB-F5 antibody has V domains defined by the following polypeptide sequences:

H chain V domain: EEQLVESGGGLVKPGGSL-RLSCAASGFSFSDCRMYWLRQA PGKGLEWIGVIS-VKSENYGANYAESVRGRFTIS-RDDSKNTVYLQMNSLKTEDTAVYYCS ASYYRYDVGAWFAYWGQGTLVTVSS (SEQ ID NO: 1)

L chain V domain: DIVMTQSPDSLAVSLGERATIN-CRASKSVSTSGYSYIYWYQQ KPGQPPKLLIY-LASILESGVPDRFSGSGSGTDFTLTISS-LQAEDVAVYYCQHSRELPWTFG QGTKVEIK (SEQ ID NO: 2).

Generally, ahB-F5 antibody of the invention further comprises a human constant region (Fc). This constant region can be selected among constant domains from any class of immunoglobulins, including IgM, IgG, IgD, IgA and IgE, and any isotype, including IgG1, IgG2, IgG3 and IgG4. Preferred constant regions are selected among constant domains of IgG, in particular IgG1.

The present invention also includes any fragment of an hB-F5 antibody comprising the V regions thereof. This comprises in particular Fab, Fab', F(ab)'2, Fv and scFv fragments.

The invention also encompasses a polynucleotide selected among:
a polynucleotide encoding a polypeptide of SEQ ID NO: 1
a polynucleotide encoding a polypeptide of SEQ ID NO: 2.

Preferably, said polynucleotide is selected among:
a polynucleotide of SEQ ID NO a: 3;
a polynucleotide of SEQ ID NO: 4.

Polynucleotides of the invention can easily be obtained by the well-known methods of recombinant DNA technology and/or of chemical DNA synthesis.

A polynucleotide encoding the V domain of the H chain or of the L chain of a hB-F5 antibody may be fused with a polynucleotide coding for the constant region of a human H or L chain, for the purpose of expressing the complete H and L chains obtained in this way; a sequence coding a signal peptide allowing the secretion of the protein can also be added. These recombinant polynucleotides are also part of the invention.

The invention also provides expression cassettes wherein a polynucleotide of the invention is linked to appropriate control sequences allowing the regulation of its transcription and translation in a chosen host cell, and recombinant vectors comprising a polynucleotide or an expression cassette of the invention.

These recombinant DNA constructs can be obtained and introduced in host cells by the well-known techniques of recombinant DNA and genetic engineering.

The invention also comprises a host cell, transformed by a polynucleotide of the invention.

Useful host-cells within the framework of the present invention can be prokaryotic or eukaryotic cells. Among suitable eukaryotic cells, one will mention, by way of example, plant cells, cells of yeasts such as Saccharomyces, cells of insects such as Drosophila, or Spodoptera, and mammal cells such as HeLa, CHO, 3T3, C127, BHK, COS, etc. . . . .

The construction of expression vectors of the invention, and the transformation of host-cells can be made by the standard techniques of molecular biology.

An hB-F5 antibody of the invention can be obtained by culturing a host cell containing an expression vector comprising a nucleic acid sequence encoding said antibody, under conditions suitable for the expression thereof, and recovering said antibody from the host cell culture.

The present invention also comprises a therapeutic composition comprising a hB-F5 antibody of the invention or a fragment thereof, as defined above.

Preferably, said composition is a composition for parenteral administration, formulated to allow the administration of a dose of from 0.1 to 10 mg, advantageously of from 1 to 5 mg of hB-F5.

More specifically, the invention encompasses the use of an hB-F5 antibody of the invention or a fragment thereof, for preparing an immunosuppressive composition. Said immunosuppressive composition is useful in particular for the treatment or prevention of diseases such as graft rejection, graft-versus-host reaction or host-versus-graft reaction, or autoimmune diseases including for instance myocarditis, diabetes mellitus, psoriasis, lupus erythematosus, Crohn's disease, multiple sclerosis, rheumatoid arthritis, etc.

Moreover, the inventors have found out that hB-F5 was able to activate a particular subset of T CD4+ cells, namely CD4+CD25+ cells.

CD25+CD4+ regulatory T cells (Treg cells) constitute 5-10% of peripheral CD4+ T cells. They were first described in 1995 by Sakaguchi et al. (J. Immunol., 155: 1151-1164) as regulatory cells in mice. When activated, these cells are able to suppress both CD4+ and CD8+ T cell activation and proliferation. Later, CD25+CD4+ suppressor T cells have also been found in humans (Jonuleit et al., J. Exp. Med. 193, 1285-1294, 2001; Levings et al., J. Exp. Med. 193, 1295-1302, 2001; Dieckmann et al., J. Exp. Med. 193, 1303-1310 2001). Numerous articles have been published describing the immunosuppressive role of these cells in different autoimmune disease models and in vitro systems (for review, see for instance Shevach, J. Exp. Med., 193, 11, 41-46, 2001). Ex vivo activated CD4+CD25+ Treg cells have also been shown to be effective at preventing graft-versus-host disease (Taylor et al., Blood, 99, 3493-3499, 2002; Cohen et al., J. Exp. Med. 196,401-406, 2002; Hoffmann et al., J. Exp. Med. 196,389-399, 2002). Thus, providing means for activating CD4+ CD25+ Treg cells is of great interest.

The invention also relates to the use of the hB-F5 antibody of the invention, or of the parent antibody B-F5, to activate in vitro CD25+CD4+ regulatory T cells.

Preferably, the hB-F5 antibody of the invention is added to the CD25+CD4+ regulatory T cells at a concentration 1 µg/ml from 10 µg/ml.

EXAMPLES

The present invention will be further illustrated by the following additional description, which refers to examples illustrating the properties of hB-F5 antibodies of the invention. It should be understood however that these examples are given only by way of illustration of the invention and do not constitute in any way a limitation thereof.

Example 1

Construction of Humanized B-F5

Design of Humanized B-F5 VH and VK Regions

DNA sequences encoding mouse B-F5 $V_H$ and $V_K$ regions are respectively shown in FIG. 1 and FIG. 2 and under sequence identifiers SEQ ID NO: 5 and SEQ IN ISO: 6. The human $V_H$ and $V_K$ on which the mouse CDRs are grafted were selected by searching databases for human $V_H$ most like the original mouse B-F5 $V_H$ and $V_K$. $V_H$ region of a human antibody (M26; Accession Number A36006) had the highest homology with B-F5 $V_H$. $V_K$ region of another human antibody (FK-001; NAKATANI et al., Biotechnology, 7 (1989), 805-810)) had the highest homology with B-F5 $V_K$.

Two types of $V_K$ differing between them in that the 4th residue was Leucine or Methionine were constructed and designated as L4L and L4M. Two types of VH differing between them in that the 37th amino acid residue was Leucine or Valine, were constructed and designated as H37L and H37V. The alignment of the polypeptide sequences of B-F5, FK-001, L4L, and L4M is shown in FIG. 3. The alignment of the polypeptide sequences of B-F5, M26, H37L, and H37V is shown in FIG. 4. The FR residues previously reported to be important for the packing of CDRs (Chothia et al., Nature, 342 (1989), 877; Foote et al., J. Mol. Biol., 224 (1992), 487) are boxed.

By combining these VH and VK, 4 versions of V regions were designed.

Expression of Humanized B-F5

The subsequent steps for production of humanized B-F5 were the same as those disclosed in U.S. Pat. No. 5,886,152 for humanized B-B10.

Briefly, expression plasmids for the H chain (VH humanized region fused to the constant region of a humany-1 chain (TAKAHASHI et al., Cell, 29 (1982), 671-679)) and the L chain (VK humanized region fused to the constant region of FK-001K chain) of humanized B-F5 were constructed separately. In these plasmids, the expression of humanized B-F5 is driven by the promoter/enhancer of the gene of human monoclonal IgM, FK-001. FIGS. 5 and 6 respectively show the fragments of the plasmids encoding the VH and VK regions of humanized BF-5. The sequences encoding the V region are underlined and the corresponding polypeptide sequences are indicated above the nucleotide sequence. Both plasmids and pSV2neo were simultaneously introduced into mouse myeloma Sp2/0 (ATCC CRL-1581) using Lipofectin. Transfectomas producing human IgG were selected by ELISA, using an anti-human IgG(y chain) antibody and an anti-human Ig K chain antibody.

Example 2

Characterisation of the Different Versions of Humanized B-F5 Estimation of CD4 Binding Activity Culture supernatants of transfectomas producing the four versions of hB-F5 were collected, and concentrated. The different antibodies were purified from culture supernatants by affinity chromatography using protein A Sepharose and assessed for their CD4 binding activity by measuring, by means of competitive ELISA, their inhibitory activities against the binding of biotinylated mB-F5 to soluble CD4 coated on microtiter plates. Incubation time is 2 hours for 37 C and overnight for 4 C.

The relative binding activities of hB-F5s (binding activity of mB-F5 was taken as 100%) are shown in Table I below

TABLE I

| Antibody | Temp (° C.) | Relative binding activity (% of mB-F5) |
|---|---|---|
| H37L/L4L | 4 | 80 |
|  | 37 | 30 |
| H37L/L4M | 4 | 80 |
|  | 37 | 30 |
| H37V/L4L | 4 | 10-20 |
|  | 37 | 10 |
| H37V/L4M | 4 | 10-20 |
|  | 37 | 10 |

From the results shown in Table I, it appears that the 37th residue of $V_H$, Leucine, is critical to maintain CD4 binding activity of hB-F5 because the CD4 binding activity is several-fold reduced by conversion of $^{37}$Leu to $^{37}$Val. On the contrary, the $4^{th}$ residue of V□ is found to be not so important for the CD4 binding activity. As the structural difference between $^{37}$Leu and $^{37}$Val of $V_H$ is not clearly demonstrated by molecular modeling, the superiority of H37L to H37V in CD4 binding activity was unexpected.

H37L/L4L and H37L/L4M were chosen for evaluating the in vitro biological activities.

Investigation of the in vitro biological activities of humanized B-F5

The in vitro biological activities of mouse B-F5 and humanized B-F5s (H37L/L4M IgG1 and H37L/L4L IgG 1) were evaluated. Humanized B-F5s of IgG2 type (H37L/L4M IgG2 and H37L/L4L IgG2) were also tested.

The in vitro biological activities of mB-F5 and the four types of hB-F5s were evaluated using peripheral blood mononuclear cells (PBMCs) from healthy donors. PBMCs were activated by ConA (2.5 µg/ml, 3 days) of PPD (10 µg/ml, 4 days) in the presence of murine or hB-F5s, and were monitored for their proliferative responses by $^3$H-thymidine incorporation.

Figure 8:
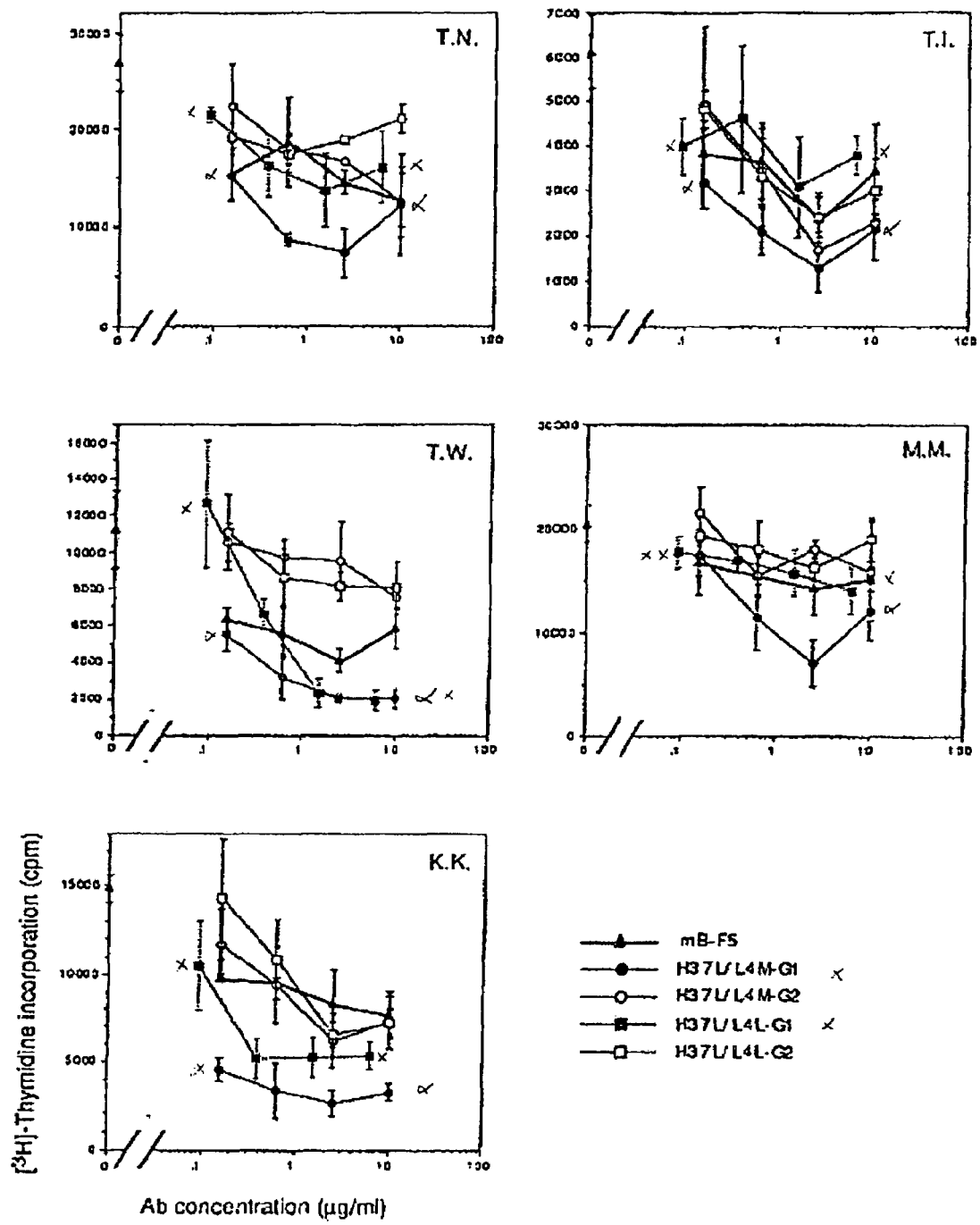
FIG. 8 shows the results of the ELISA assays, wherein murine and hB-F5s were able to inhibit Ag-specific PBMC proliferation induced by PPD.

The results are shown in FIGS. 7 and 8. Murine and hB-F5s could moderately inhibit ConA-induced proliferation, but the activities varied from antibody to antibody and/or from donor to donor (FIG. 7). Also, murine and hB-F5s were able to inhibit Ag-specific PBMC proliferation induced by PPD (FIG. 8).

IgG1 type of hB-F5 inhibited PPD-induced proliferation more effectively (as high as 70% inhibition, FIGS. 7 and 8) than Mb-F5. IgG1 type seemed to be more effective than IgG2 type of which inhibitory activity was almost the same as mB-F5. For IgG2 type of H37L/L4M and H37L/L4L inhibitory activities of B-F5s against PPD-induced PMBC proliferation were as follows: H37L/L4M IgG1>H37L/L4L IgG1>H37L/L4M IgG2=H37L/L4L IgG2=mB-F5.

Considering the efficacy of the in vitro biological activity and the smaller number of mouse amino acids, H37L/L4M IgG1 was chosen for further evaluation.

Example 3

Preliminary Evaluation of the Effect of hB-F5 on Patients with Reheumatoid Arthritis (RA)

The effect of hB-F5 (H37L/L4M IgG1) was tested on RA patients.

The conditions of the assay are as follows:

Each patient received a 10 days treatment consisting of 5 injections of 5 mg of hB-F5 (an injection every 2nd day).

The results for 3 different patients are shown in Tables II-IV below:

Patient 1 (Table II):

Diagnosis: Rheumatoid Arthritis, Activity 2

Rheumatoid factor: 2; Stage: 2

Sex: F; Age: 65; Onset of the disease: 1965

Additional therapy: Diclophenac 150 mg/day

TABLE II

| Clinical Investigations | Before Treatment | During treatment (days) | | | | | After treatment (weeks) |
|---|---|---|---|---|---|---|---|
| | | 2 | 4 | 6 | 8 | 10 | 4 |
| Estimation of pain in joints (0-10) | 4.5 | 2 | 2 | 1.5 | 3 | 2.2 | 3.5 |
| Morning stiffness in minutes | 360 | 0 | 0 | 90 | 90 | 120 | 20 |
| Severity of condition (1-5) | | | | | | | |
| Physician | 3 | 3 | 3 | 2.5 | 3 | 3 | 3 |
| Patient | 3 | 3 | 3 | 3 | 3 | 3 | 3 |
| Number of swollen joints | 6 | 6 | 4 | 3 | 2 | 2 | 7 |
| Number of painful joints | 25 | 12 | 6 | 7 | 13 | 13 | 23 |
| Swelling index (0-30) | 8 | 6 | 4 | | 2 | 3 | 9 |
| Power in hand | | | | | | | |
| Right | 17 | 15 | 20 | 22 | 12 | 20 | 15 |
| Left | 10 | 10 | 10 | 15 | 12 | 19 | 12 |
| Estimation of tiredness (0-10) | 7.7 | 4 | 2.3 | 2 | 2.3 | 3.1 | 3 |
| Estimation of treatment effects | | | | | | | |
| Patent | | 3 | 3 | 4 | 3 | 5 | 2 |
| Physician | | 3 | 3 | 4 | 3 | 5 | 2 |
| Erythrocyte sedimentation rate | 35 | | | | | 34 | 25 |
| C-Reactive Protein | 4.0 | | | | | 2 | 2.5 |

Patient 2 (Table III):

Diagnosis: Rheumatoid Arthritis, Activity 3

Rheumatoid factor: 2; Stage: 2

Sex: F; age: 48 Onset of the disease: 2000

Additional therapy. Diclophenac 150 mg/day

TABLE III

| Clinical Investigations | Before Treatment | During treatment (days) | | | | | After treatment (weeks) |
|---|---|---|---|---|---|---|---|
| | | 2 | 4 | 6 | 8 | 10 | 4 |
| Estimation of pain in joints (0-10) | 8.2 | 8.2 | 5 | 2.9 | 2.2 | 0.6 | |
| Morning stiffness in minutes | 240 | 120 | 120 | 60 | 20 | 10 | |
| Severity of condition (1-5) | | | | | | | |
| Physician | 4 | 3 | 3 | 3 | 3 | 2 | |
| Patient | 4 | 4 | 3 | 3 | 3 | 2 | |
| Number of swollen joints | 13 | 12 | 11 | 11 | 5 | 5 | |
| Number of painful joints | 22 | 22 | 16 | 15 | 13 | 7 | |
| Swelling index (0-30) | 15 | 14 | 12 | 11 | 5 | 5 | |
| Power in hand | | | | | | | |
| Right | 30 | 30 | 28 | 34 | 36 | 40 | |
| Left | 22 | 20 | 18 | 18 | 22 | 28 | |
| Estimation of tiredness (0-10) | 8.7 | 5.1 | 2.2 | 2.2 | 1.1 | 0.7 | |
| Estimation of treatment effects | | | | | | | |
| Patent | | 3 | 4 | 4 | 4/5 | 5 | |
| Physician | | 3 | 2 | 3 | 4/5 | 5 | |
| Erythrocyte sedimentation rate | 35 | | | | | 38 | 35 |
| C-Reactive Protein | 1.2 | | | | | 0.2 | 0.8 |

Patent 3 (Table IV):

Diagnosis: Rheumatoid Arthritis, Activity 3

Rheumatoid factor: 3; Stage: 2

Sex: F; Age: 49; Onset of the disease: 1989

Additional therapy. Diclophenac 150 mg/day

3) Test System:

CD25+ Tregs from donor A are cocultured for 2 days with syngenicCD2-depleted PBMC, without additions (negative control=no activation=no suppressive activity), or in the presence of 0.5 µg/ml anti-CD3 (OKT-3=positive control=full activation of Tregs), or in the presence of 5 µg/ml or 30 µg/ml hB-F5.

TABLE IV

| Clinical Investigations | Before Treatment | During treatment (days) | | | | | After treatment (weeks) | |
|---|---|---|---|---|---|---|---|---|
| | | 2 | 4 | 6 | 8 | 10 | 1 | 2 |
| Estimation of pain in joints (0-10) | 7.9 | 7.6 | 7.6 | 7.2 | 5.0 | 3.0 | 1.5 | 1.3 |
| Morning stiffness in minutes | 360 | 0 | 0 | 0 | 0 | 0 | 0 | |
| Severity of condition (1-5) | | | | | | | | |
| Physician | 4 | 3 | 3 | 3 | 3 | 3 | 2 | 2 |
| Patient | 5 | 4 | 4 | 3 | | 3 | 2 | 2 |
| Number of swollen joints | 10 | 7 | 7 | 6 | 5 | 5 | 5 | 5 |
| Number of painful joints | 30 | 24 | 24 | 15 | 11 | 11 | 10 | 9 |
| Swelling index (0-30) | 15 | 12 | 12 | 9 | 7 | 7 | 6 | |
| Power in hand | | | | | | | | |
| Right | 24 | 30 | 30 | 36 | 48 | 48 | 50 | 50 |
| Left | 24 | 30 | 30 | 38 | 40 | 34 | 40 | 42 |
| Estimation of tiredness (0-10) | 8.5 | 7.2 | 5.2 | 0 | 0 | 0 | 0 | 0 |
| Estimation of treatment effects | | | | | | | | |
| Patent | | 3 | 3 | 3 | | 5 | 5 | 5 |
| Physician | | 3 | 4/3 | 4 | 4 | 5 | 5 | 5 |
| Erythrocyte sedimentation rate | 61 | | 53 | 42 | 45 | | | 41 |
| C-Reactive Protein | 8 | | | | 3.7 | | | 3.3 |

Example 4

Activation of CD4+CD25+ Treg Cells by hB-F5

Isolation of T cells:

1) T regulatory cells (Tregs):

CD25+ cells are isolated using CD25 microbeads;

Depletion of contaminations: CD14-, CD8-, CD19-positive cells is made with CD 14/CD8/CD19DYNALbeads;

Depletion of CD45RA+ cells is made with CD45RA mAb+anti-mouse DYNALbeads: purity: >95% CD4+CD25+ Tregs 2) Effector Cells CD4+T cells are isolated using CD4 microbeads Depletion of CD45RO+ cells is made with CD45RO+ mAb+anti-mouse DYNALbeads; purity: >98% CD4/CD45RA+, CD25- effector T cells After extensive washing of pre-cultured cells, CD25+ Tregs cells are isolated and treated by γ-radiation (3000 rad).

4) Test of Suppressive Activity:

Pre-cultured CD25+ Tregs cells are cocultured for 4 days with freshly isolated CD4+ effector T cells(1:1) from donor B in the presence of APC's (CD2-depleted PBMC) from donor A (syngenic for pre-cultured T cells (no additional activation), allogeneic for effector T cells (=allogeneic mixed lymphocyte reaction). Then, cells are incubated for 16 h with 3H Thymidine, and proliferation of effector T cells is detected.

Figure 9:
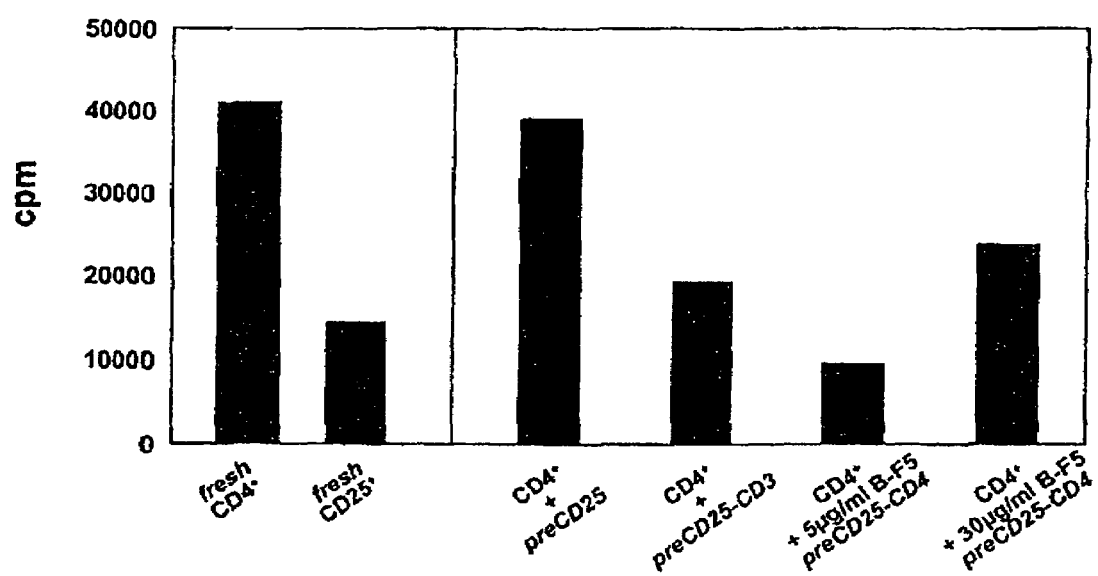
FIG. 9 shows a test of suppressive activity, wherein the negative control (no activation) is preCD25; 0.5 µg/ml OKT-3 (positive control, full activation) is preCD25-CD3; 5 µg/ml hB-F5 (Test 1) is preCD25-CD4; 30 µg/ml hB-F5 (Test 2) is preCD25-CD4.

The results are shown in FIG. 9.

Legend of FIG. 9:

negative control (no activation)=preCD25;

0.5 µg/ml OKT-3 (positive control, full activation)=preCD25-CD3;

5 µg/ml hB-F5(Test-1)=preCD25-CD4;

30 µg/ml hB-F5 (Test-2)=preCD25-CD4.

What is claimed is:

1. A humanized hB-F5 antibody derived from mouse monoclonal anti-CD4 antibody B-F5, wherein said hB-F5 antibody comprises V domains comprising:
   a) an H chain V domain comprising the sequence, EEQLVESGGGLVKPGGSLRLSCAASGFSFSDCRMYWLRQAPGKGLEWIGVISVKSENYGANYAESVRGRFTISRDDSKNTVYLQMNSLKTEDTAVYYCSASYYRYDVGAWFAYWGQGTLVTVSS (SEQ ID NO: 1); and
   b) a L chain V domain comprising the sequence: DIVMTQSPDSLAVSLGERATINCRASKSVSTSGYSYIYWYQQKPGQPPKLLIYLAS ILESGVPDRFSGSGSGTDFTLTISSLQAEDVAVYYCQHSRELPWTFGQGTKVEIK (SEQ ID NO: 2), wherein said bB-F5 antibody is able to activate a subset of T CD4$^+$ cells comprising CD4$^+$CD25$^+$ cells.

2. A fragment of the hB-F5 antibody of claim 1, wherein said fragment comprises the V domains of SEQ ID NO: I and SEQ ID NO: 2.

3. A therapeutic composition comprising a humanized antibody of claim 1, or a fragment of the hB-F5 antibody of claim 1, wherein said fragment comprises the V domains of SEQ ID NO: I and SEQ ID NO: 2.

4. A method comprising:
   preparing an immunosuppressive composition comprising the humanized antibody of claim 1, or a fragment of the hB-F5 antibody of claim 1;
   wherein said fragment comprises the V domains of SEQ ID NO: 1 and SEQ ID NO: 2.

\* \* \* \* \*

SEQUENCE LISTING

<160> NUMBER OF SEQ ID NOS: 6

<210> SEQ ID NO 1
<211> LENGTH: 124
<212> TYPE: PRT
<213> ORGANISM: Artificial sequence
<220> FEATURE:
<223> OTHER INFORMATION: V domain of H chain of humanized antibody hBF-5

<400> SEQUENCE: 1

```
Glu Glu Gln Leu Val Glu Ser Gly Gly Gly Leu Val Lys Pro Gly Gly
 1               5                  10                  15

Ser Leu Arg Leu Ser Cys Ala Ala Ser Gly Phe Ser Phe Ser Asp Cys
            20                  25                  30

Arg Met Tyr Trp Val Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60

Ser Val Arg Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Ala Ser Tyr Tyr Arg Tyr Asp Val Gly Ala Trp Phe Ala
            100                 105                 110

Tyr Trp Gly Gln Gly Thr Leu Val Thr Val Ser Ser
        115                 120
```

<210> SEQ ID NO 2
<211> LENGTH: 111
<212> TYPE: PRT
<213> ORGANISM: Artificial sequence
<220> FEATURE:
<223> OTHER INFORMATION: V domain of K chain of humanized antibody hBF-5

<400> SEQUENCE: 2

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
            20                  25                  30

Gly Tyr Ser Tyr Ile Tyr Trp Tyr Gln Gln Lys Pro Gly Gln Pro Pro
        35                  40                  45

Lys Leu Leu Ile Tyr Leu Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Trp Thr Phe Gly Gln Gly Thr Lys Val Glu Ile Lys
            100                 105                 110
```

<210> SEQ ID NO 3
<211> LENGTH: 372
<212> TYPE: DNA
<213> ORGANISM: Artificial sequence
<220> FEATURE:
<223> OTHER INFORMATION: V domain of H chain of humanized antibody hBF-5

<400> SEQUENCE: 3
gaggaacagc ttgtggagtc tgggggaggc ttggtgaaac ccggaggttc tctgaggctc      60

```
tcctgtgcag cctcgggttt cagtttcagt gactgccgga tgtactgggt tcgccaggct    120
ccagggaagg ggctggagtg gattggtgtg atttcagtca aatctgagaa ttatggagca    180
aattatgcag agtctgtgag gggcagattc actatttcaa gagatgattc aaaaaacacg    240
gtctatctgc agatgaacag cttgaagacc gaagacactg ccgtttatta ttgtagtgcc    300
tcctattata ggtacgacgt gggggcctgg tttgcttact ggggccaagg gactctggtc    360
actgtctctt ca                                                        372
```

<210> SEQ ID NO 4
<211> LENGTH: 336
<212> TYPE: DNA
<213> ORGANISM: Artificial sequence
<220> FEATURE:
<223> OTHER INFORMATION: V domain of K chain of humanized antibody hBF-5

<400> SEQUENCE: 4

```
gacatcgtga tgacccagtc tccagactcc ctggctgtgt ctctgggcga gagggccacc    60
atcaactgca gggccagcaa aagtgtcagt acatctggct acagttatat atattggtac    120
cagcagaaac aggacagcc tcctaagctg ctcatttacc ttgcatccat cctagaatct    180
ggggtccctg accgattcag tggcagcggg tctgggacag atttcactct caccatcagc    240
agcctgcagg ctgaagatgt ggcagtttat tactgtcagc acagtaggga acttccgtgg    300
acgttcggcc aagggaccaa ggtggaaatc aaacgt                              336
```

<210> SEQ ID NO 5
<211> LENGTH: 372
<212> TYPE: DNA
<213> ORGANISM: Mus musculus

<400> SEQUENCE: 5

```
caggaatacc ttgtggagac cgggggaggc ttggtgaggc ctggaaattc tctgaaactc    60
tcctgtgtca cctcgggttt cagtttcagt gactgccgga tgtactggct cgccagcct    120 ccagggaagg ggctggagtg gattggtgtg atttcagtca aatctgagaa ttatggagca    180
aattatgcag agtctgtgag gggcagattc actatttcaa gagatgattc aaaaagcagt    240
gtctatctgc agatgagcag attgagagag gaagacactg ccacttatta ttgtagtgcc    300
tcctattata ggtacgacgt gggggcctgg tttgcttact ggggccaagg gactctggtc    360
actgtctctg ca                                                        372
```

<210> SEQ ID NO 6
<211> LENGTH: 383
<212> TYPE: DNA
<213> ORGANISM: Mus musculus

<400> SEQUENCE: 6

```
gacattgtgc tgacacagtc tccttcttcc ttagttgtat ctctggggca gagggccacc    60
atctcatgca gggccagcaa aagtgtcagt acatctggct acagttatat atattggtac    120
caacagatcc caggacagcc acccaaactc ctcatctatc ttgcatccat cctagaatct    180
ggggtccctg caggttcag tggcagtggg tctgggacag acttcaccct caacatccat    240
cctgtggagg aggaggatgc tgcaacctat tactgtcagc acagtaggga acttccgtgg    300
acgttcggtg gaggcaccaa gctggagatc aaacggctg atgctgcacc aactgtatcc    360
atcttcccac catccagtga gca                                            383
```